US008805488B2

(12) United States Patent
Grady

(10) Patent No.: US 8,805,488 B2
(45) Date of Patent: Aug. 12, 2014

(54) AUTOMATED ISCHEMIA ANALYSIS OF ECG DATA

(75) Inventor: James M. Grady, Londonderry, NH (US)

(73) Assignee: Koninklijke Philips N.V., Eindhoven (NL)

( * ) Notice: Subject to any disclaimer, the term of this patent is extended or adjusted under 35 U.S.C. 154(b) by 57 days.

(21) Appl. No.: 13/202,501

(22) PCT Filed: Jan. 27, 2010

(86) PCT No.: PCT/US2010/022186
§ 371 (c)(1),
(2), (4) Date: Aug. 19, 2011

(87) PCT Pub. No.: WO2010/096246
PCT Pub. Date: Aug. 26, 2010

(65) Prior Publication Data
US 2012/0136266 A1  May 31, 2012

Related U.S. Application Data

(60) Provisional application No. 61/153,751, filed on Feb. 19, 2009.

(51) Int. Cl.
*A61B 5/04* (2006.01)

(52) U.S. Cl.
USPC ............................ 600/523; 600/509; 607/9

(58) Field of Classification Search
USPC ............. 600/508, 509, 513, 523; 607/3, 9, 22
See application file for complete search history.

(56) References Cited

U.S. PATENT DOCUMENTS

| 2003/0032871 | A1 | 2/2003 | Selker et al. | |
|---|---|---|---|---|
| 2005/0004485 | A1* | 1/2005 | Crosby et al. | 600/513 |
| 2005/0177050 | A1* | 8/2005 | Cohen | 600/509 |
| 2007/0232946 | A1 | 10/2007 | Feild et al. | |

* cited by examiner

*Primary Examiner* — Christopher D Koharski
*Assistant Examiner* — Pamela M Bays

(57) ABSTRACT

An ECG analysis system is responsive to patient ECG data for performing an analysis of the ECG data to determine whether acute MI is present. The system first analyzes the ECG data by standard ECG analysis to determine whether acute MI is present. This analysis is followed in a first mode of operation by ACI-TIPI analysis to estimate the probability of acute MI from patient characteristics and the ECG data. In a second mode, when the standard ECG analysis is definitive as to the presence of acute MI the ACI-TIPI analysis is not run and the user is presented with only the results of the standard interpretation. If the standard ECG analysis is indeterminate as to the presence of acute MI, then the ACI-TIPI analysis is run and the results of the ACI-TIPI analysis are presented to the user.

13 Claims, 17 Drawing Sheets

```
1001140641120c95      14-Jan-2010 07:51:16      50 years MALE
HR    41       Sinus bradycardia
PR    151      Inferior infarct, acute (RCA)
QRSD  99       Probable RV involvement, suggest recording right precordial leads
QT    472
QTc   390
 -- AXIS --
P     69
QRS   -10      - ABNORMAL ECG -      Unconfirmed diagnosis
T     59       Philips Predicted Probability of Acute Ischemia 37%
                        >>> Acute MI <<<
                                              MENU
```
— 182

FIG. 14

```
1001140641120c95      14-Jan-2010 07:50:00      50 years MALE
                   Candidate for Thrombolysis Time Since Onset of Ischemic Symptons        2:00
Blood Pressure                               160/100 mmHg
History of Hypertension                      Yes
History of Diabetes                          No
Patient Weight                               190 lbs.

MENU
```
— 190

FIG. 15

```
1001140641120c95      14-Jan-2010 07:50:00      50 years MALE
Consider contraindications to thrombolysis   Page 1 of 2
Right vs. left arm sys. BP difference > 15 mmHg              No
History of structural central nervous system disease         No
Significant closed head/facial trauma within prev. 3 mos.    No
Major trauma, surgery, GI/GU bleed within 6 wks              No
Bleeding or clotting problem or on blood thinners            No
CPR for longer than 10 min.                                  Yes
Prenant Female                                               No
Serious systemic disease                                     No
Pumonary edema                                               No
                              DONE       MENU
```
— 192

FIG. 16

Event ID :100114064112oc95 ID :100114064112oc95   14-Jan-2010 07:51:16   ---                          50 years MALE                    Chest Pain Primary

| | |
|---|---|
| HR   41 | Right vs. left arm sys. BP difference > 15 mmHg — No |
| PR   151 | History of structural central nervous system disease — No |
| QRSD  99 | Significant closed head/facial trauma within prev. 3 mos. — No |
| QT   472 | Major trauma, surgery, GI/GU bleed within 6 wks — No |
| QTc  390 | Bleeding or clotting problem or on blood thinners — No |
| - - AXIS - - | CPR for longer than 10 min — Yes |
| P    69 | Pregnant female — No |
| QRS  10 | Serious systemic disease — No |
| T    59 | Pulmonary edema — No |
| Signs of shock — No | |
| | >>> Acute MI <<< |

Page 7 of 7          PHILIPS          HEARTSTART MRx

FIG. 17c

AUTOMATED ISCHEMIA ANALYSIS OF ECG DATA

This application claims the benefit of U.S. provisional application Ser. No. 61/153,751, filed Feb. 19, 2009.

This invention relates to medical instruments which assist a physician in the analysis of acute ischemia and, in particular, to automated ischemia analysis of ECG data.

The Philips HeartStart® MRx monitor/defibrillator, available from Philips Healthcare of Andover, Mass., is a portable medical instrument capable of monitoring various bodily functions relating to cardiac care and is capable of providing electrotherapy such as defibrillation and pacing when needed. The MRx monitor/defibrillator is also capable of assisting medical personnel in the analysis of patient symptoms which may indicate an incidence of acute cardiac ischemia (ACI). This is done through an analysis package included in the monitor/defibrillator which is known as the Time Insensitive Predictive Instrument (ACI-TIPI) originally developed by Dr. H. P. Selker. See Selker HP, "Sorting out chest pain. Identification of acute cardiac ischemia in the emergency room setting: An approach based on the acute ischemic heart disease predictive instrument," *Emergency Decisions/Primary Care*, 1:8-17 (1985). See other papers published by Dr. Selker on ACI-TIPI in *J. Electrocardiography*, 21:S11-S17 (1988) and *Medical Care*, 29:610-627 (1991). The ACI-TIPI analysis protocol uses the patient's ECG data, symptom severity, the patient's age and gender to calculate the predicted probability that the patient has suffered acute cardiac ischemia. The ACI-TIPI analysis algorithm has previously been implemented in the Hewlett-Packard PageWriter® XLi cardiograph. The ACI-TIPI analysis is particularly useful when a patient has had a 12-lead ECG exam before the patient arrives at a hospital. The results of the analysis provide the hospital with advance notification that a patient should be rushed to an emergency catheterization procedure or other aggressive intervention, or can simply be admitted to the hospital for further tests and observation.

A 12-lead ECG exam conventionally includes a standard ECG analysis which is printed as a report at the end of the ECG strip. This standard ECG analysis can produce a definitive analysis, such as an indication of acute myocardial infarction (MI). When the standard ECG analysis is definitive, there is generally no need to perform a further ACI-TIPI analysis and the patient is immediately taken to an intervention clinic or similar care facility. The standard ECG analysis can also produce a result indicative of a normal ECG. Customarily, the ACI-TIPI analysis is typically done in addition to the standard interpretative statement analysis of the ECG data as a confirmation of the results of the standard analysis.

In this typical scenario, the ACI-TIPI analysis is generally run following the standard ECG analysis. The disadvantage of this approach is that it is possible for the ACI-TIPI analysis to calculate a predicted probability of acute MI that contradicts the results of the standard ECG analysis. In the case of an emergency medical (EMS) responder who needs an unambiguous and definitive decision as to where to transport the patient, e.g., a general hospital or specialized cardiac care treatment facility, the confusion that is introduced may delay the appropriate treatment. Accordingly it is desirable for the ECG device to operate so as to provide a clear indication of needed treatment and not present conflicting diagnostic results.

In accordance with the principles of the present invention an ECG analysis system uses the results of a standard ECG analysis to sequence the analysis of the patient data. The ACI-TIPI analysis is conducted only if the standard analysis does not produce a definitive indication that the patient has suffered acute cardiac ischemia or that the ECG is normal. The ECG analysis system is configured so that the 12-lead analysis is set to a conditional ACI-TIPI analysis setting. If the ECG analysis system is configured to perform conditional ACI-TIPI analysis following a standard 12-lead ECG analysis, then the output of the standard analysis is checked before running the ACI-TIPI analysis. If the standard analysis indicates that the ECG is a normal ECG or if it clearly indicates the presence of an acute myocardial infarction, the ACI-TIPI analysis is not run and the "Predicted Probability of Acute Cardiac Ischemia" is not displayed. If neither of these conditions exist, then the ACI-TIPI analysis is run to help the clinician with the ambiguity and the predicted probability of acute cardiac ischemia is displayed at the bottom of the ECG system display. If the ACI-TIPI analysis is run, the full ACI-TIPI report is printed as part of the 12-lead ECG report and is stored and/or printed with the patient data. The predictive indication of the probability of ACI is produced and displayed to the EMS responder in this manner for guidance as to the appropriate immediate treatment for the patient.

Figure 6A:
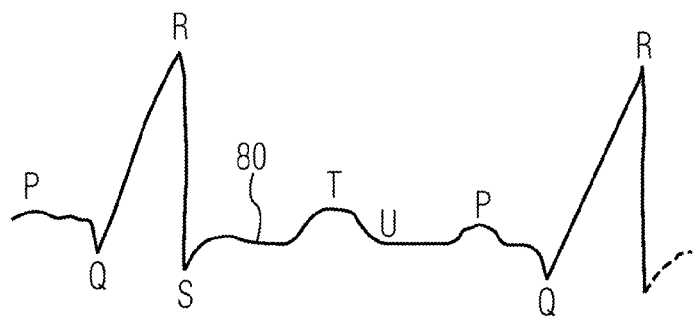
Figure 6B:
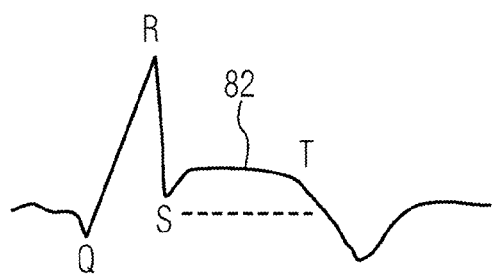

FIGS. 6*a* and 6*b* illustrate the segments of a normal ECG signal and an ECG signal exhibiting an elevated ST segment level.

Figure 7:
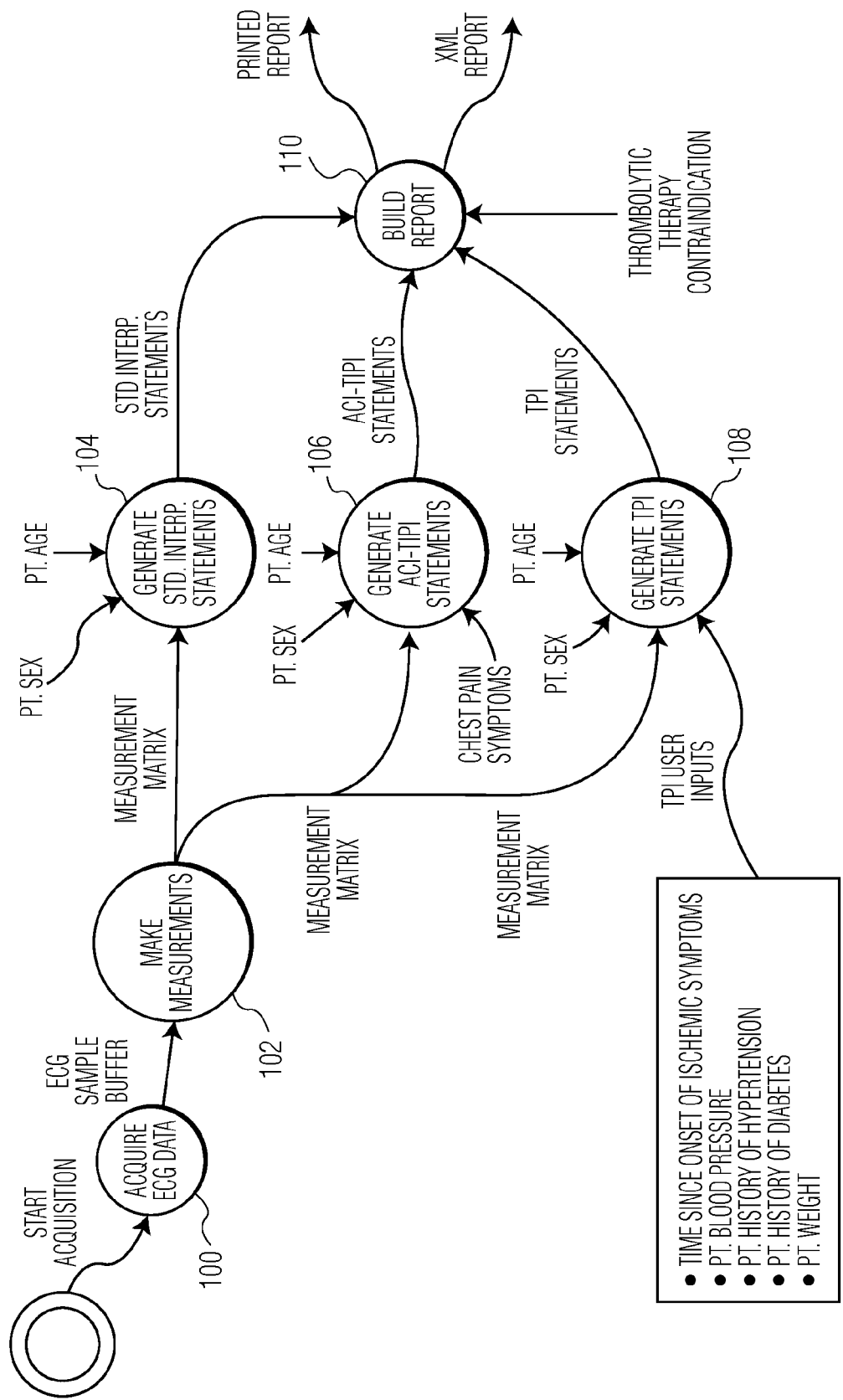

FIG. 7 is a data flow diagram showing the development of standard ECG analysis, ACI-TIPI analysis, and thrombolytic predictive instrument (TPI) analysis and reporting.

Figure 8:
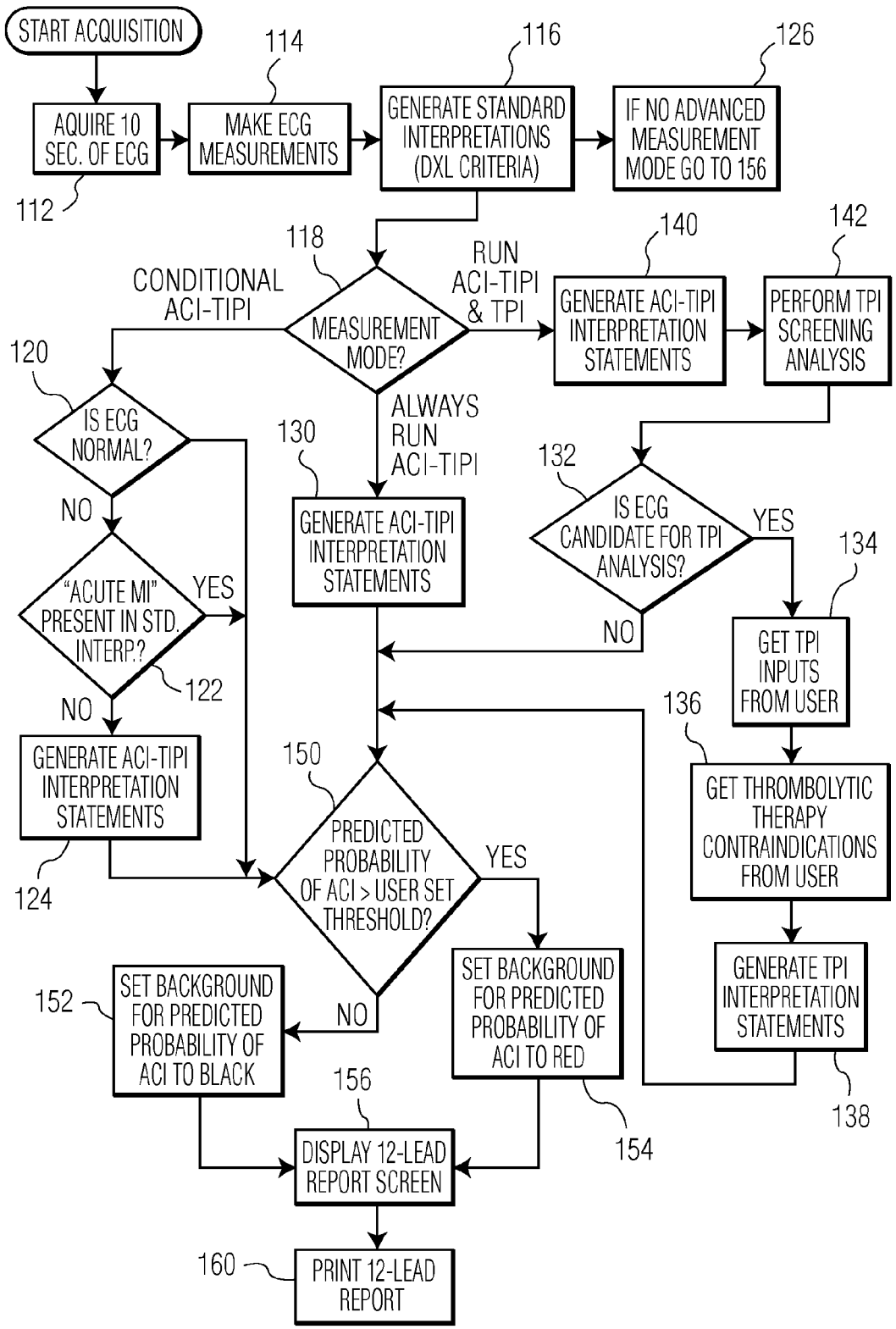

FIG. 8 is a flowchart of an implementation of conditional ACI-TIPI analysis in accordance with the principles of the present invention.

Figure 9:
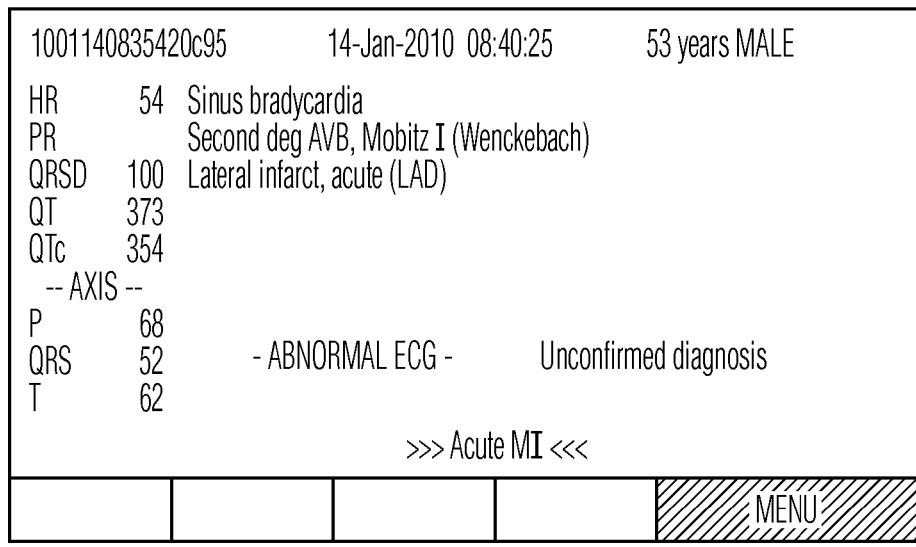

FIG. 9 illustrates a report screen of an ECG analysis system when standard ECG analysis indicates acute MI.

Figure 10:
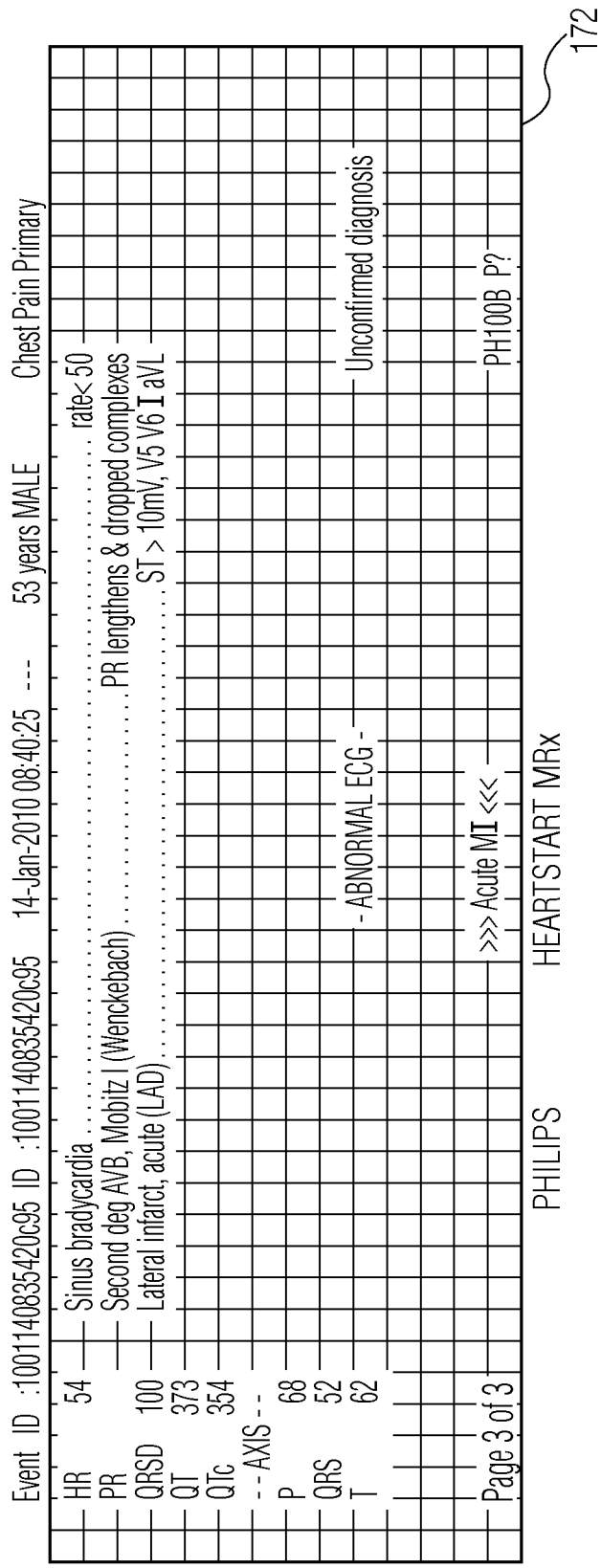

FIG. 10 illustrates an ECG strip with a standard analysis report indicating acute MI.

Figure 11:
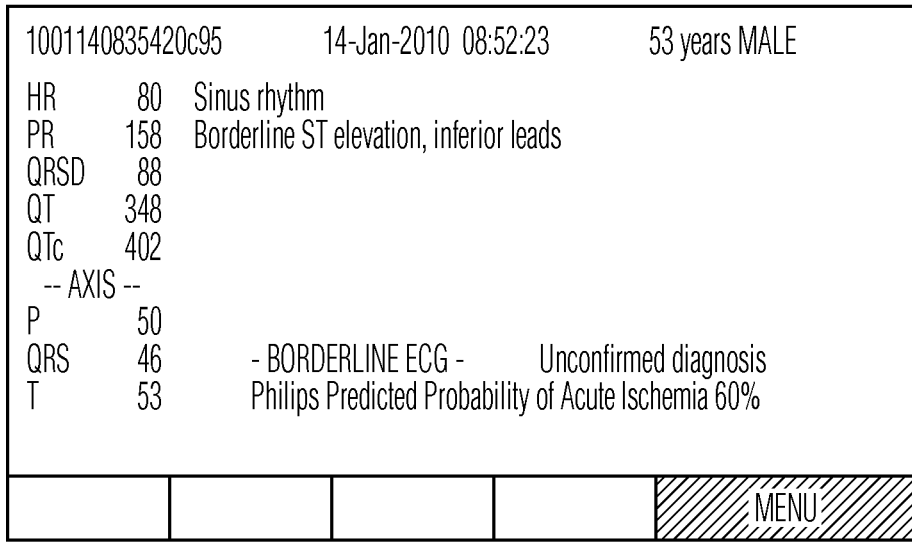

FIG. 11 illustrates the report screen when standard ECG analysis is followed by ACI-TIPI analysis.

Figure 12:
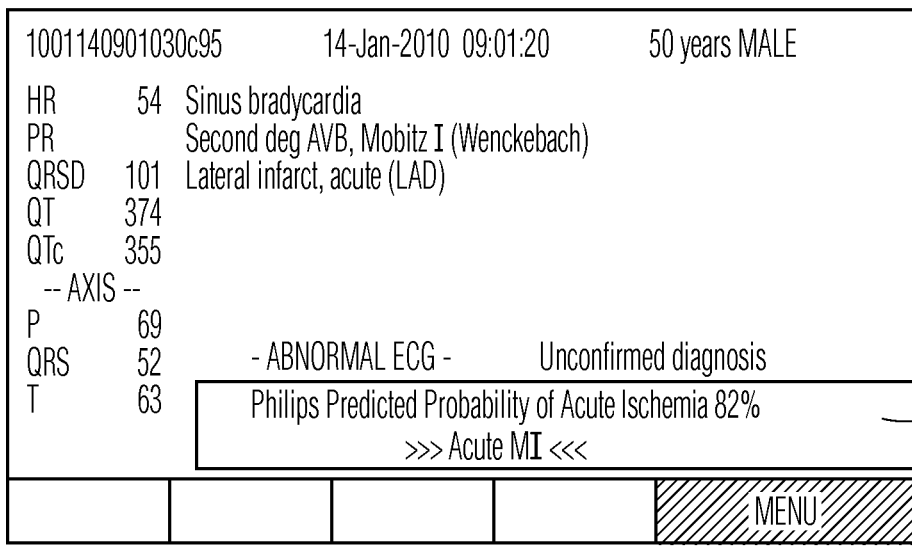

FIG. 12 illustrates the report screen when the probability of acute MI exceeds a threshold level.

Figure 13A:
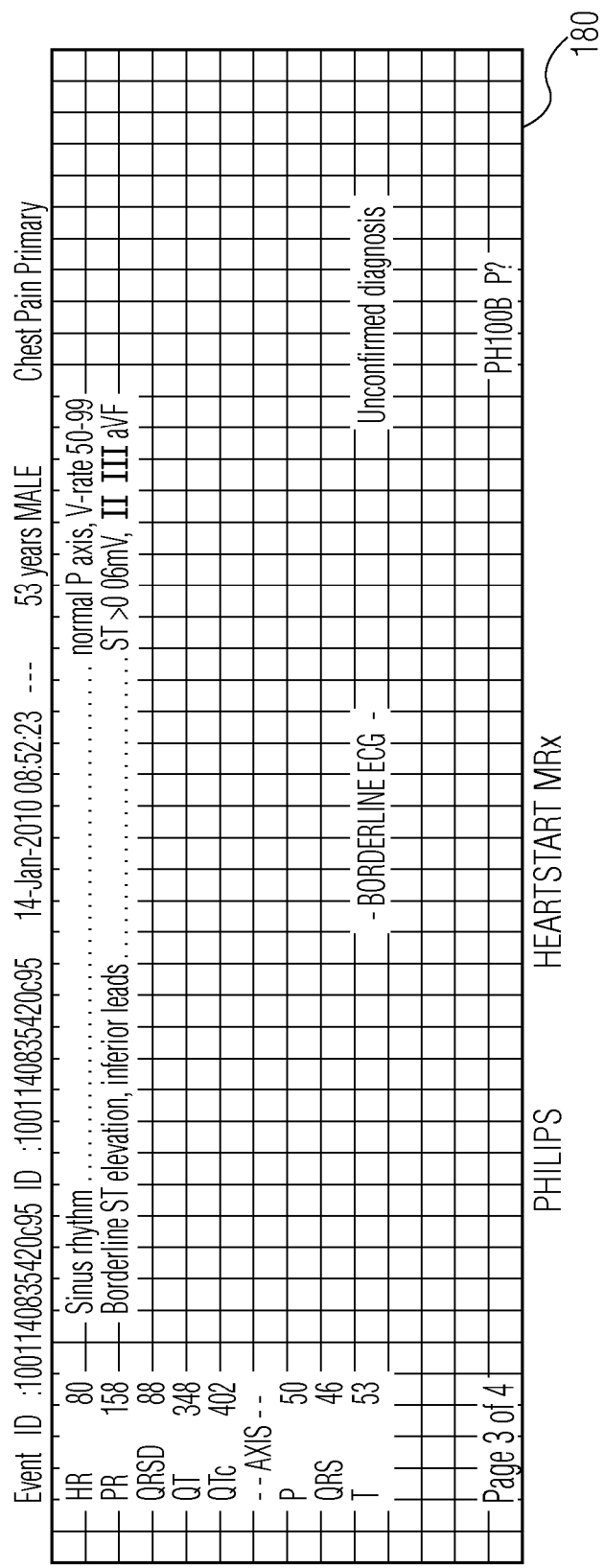
Figure 13B:
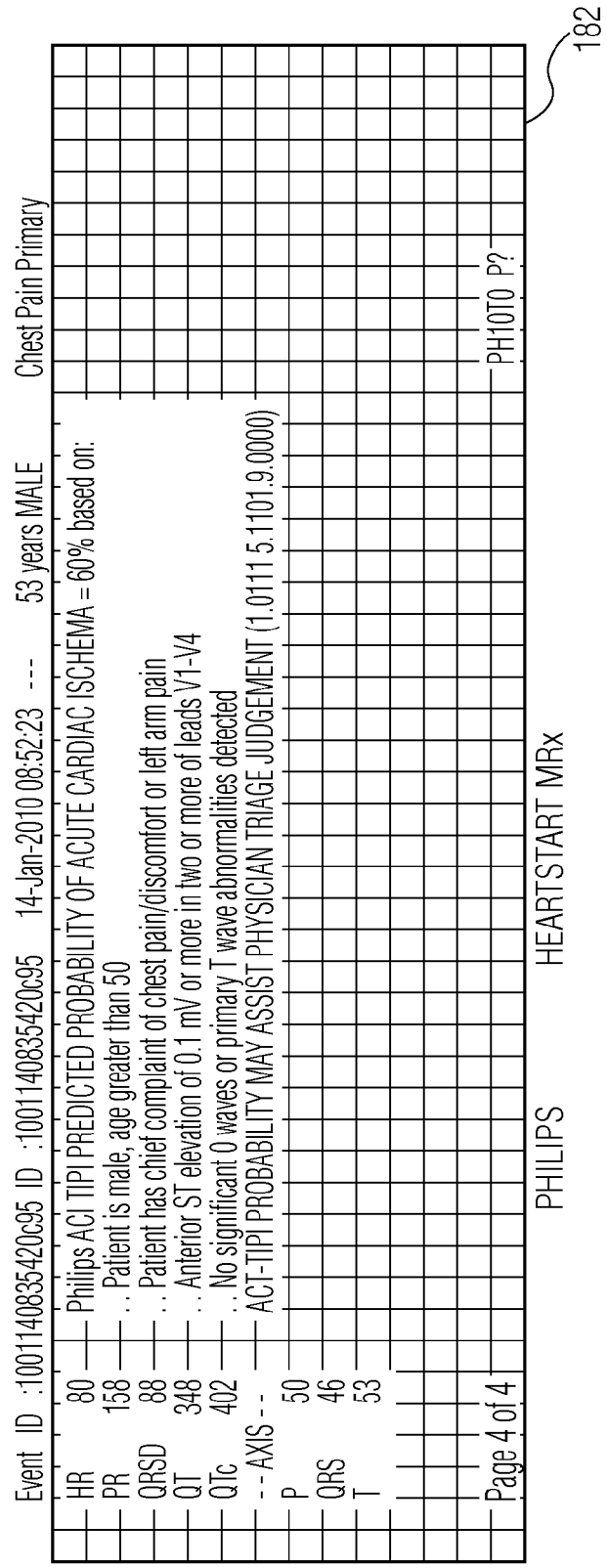

FIGS. 13*a* and 13*b* illustrate ECG strips which present a standard interpretation and ACI-TIPI statements and recommendation.

FIG. 14 illustrates the report screen when a standard ECG interpretation and ACI-TIPI analysis indicate conflicting results.

FIG. 15 illustrates prompts on the screen of an ECG analysis system which prompt a user to input data needed for TPI analysis.

FIG. 16 illustrates screen prompts for a user to consider contraindications to thrombolytic drug treatment.

Figure 17A:
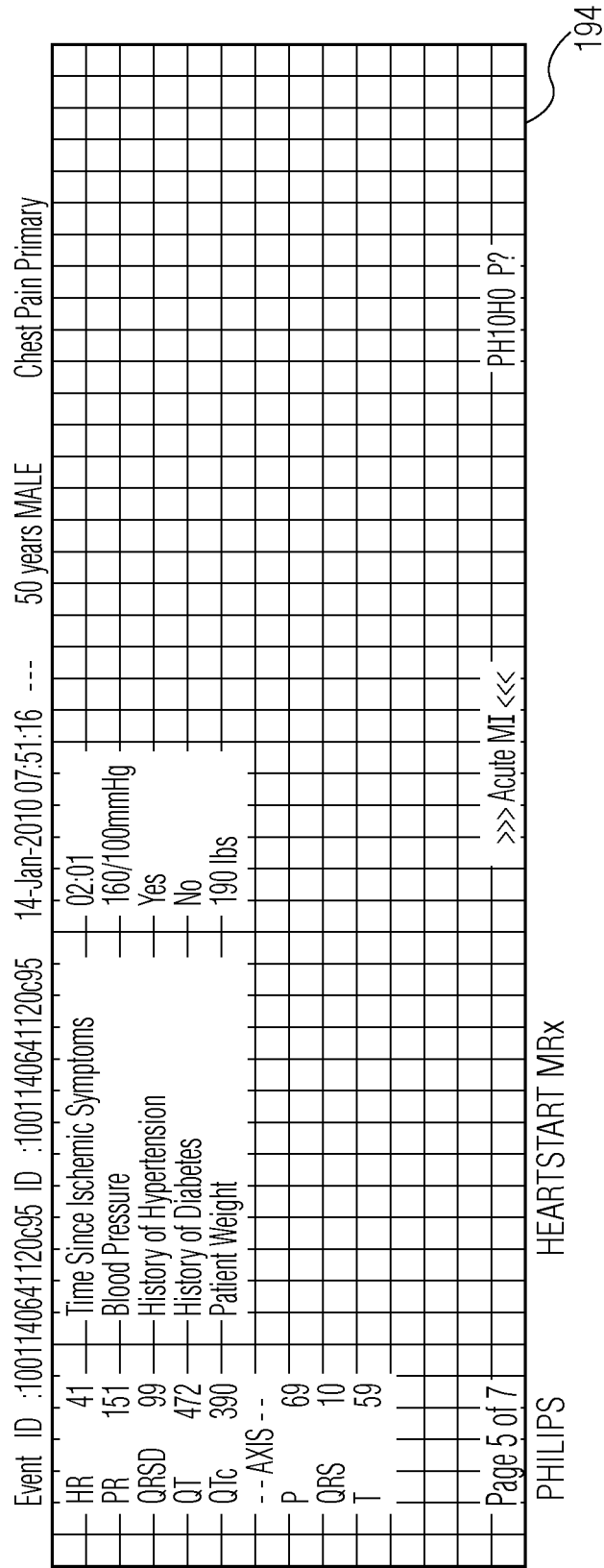
Figure 17B:
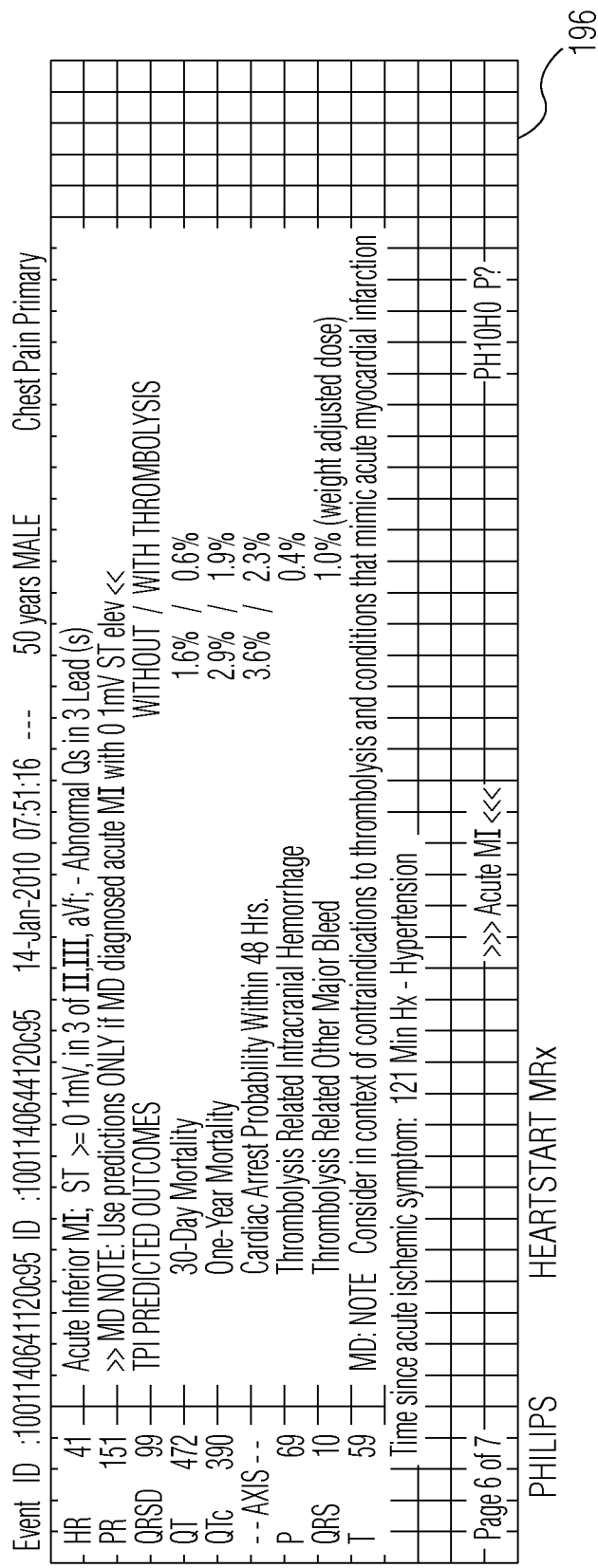

FIGS. 17*a*-17*c* illustrate an ECG strip with a printed report of TPI analysis results including the user's inputs to contraindication prompts.

Figure 1:
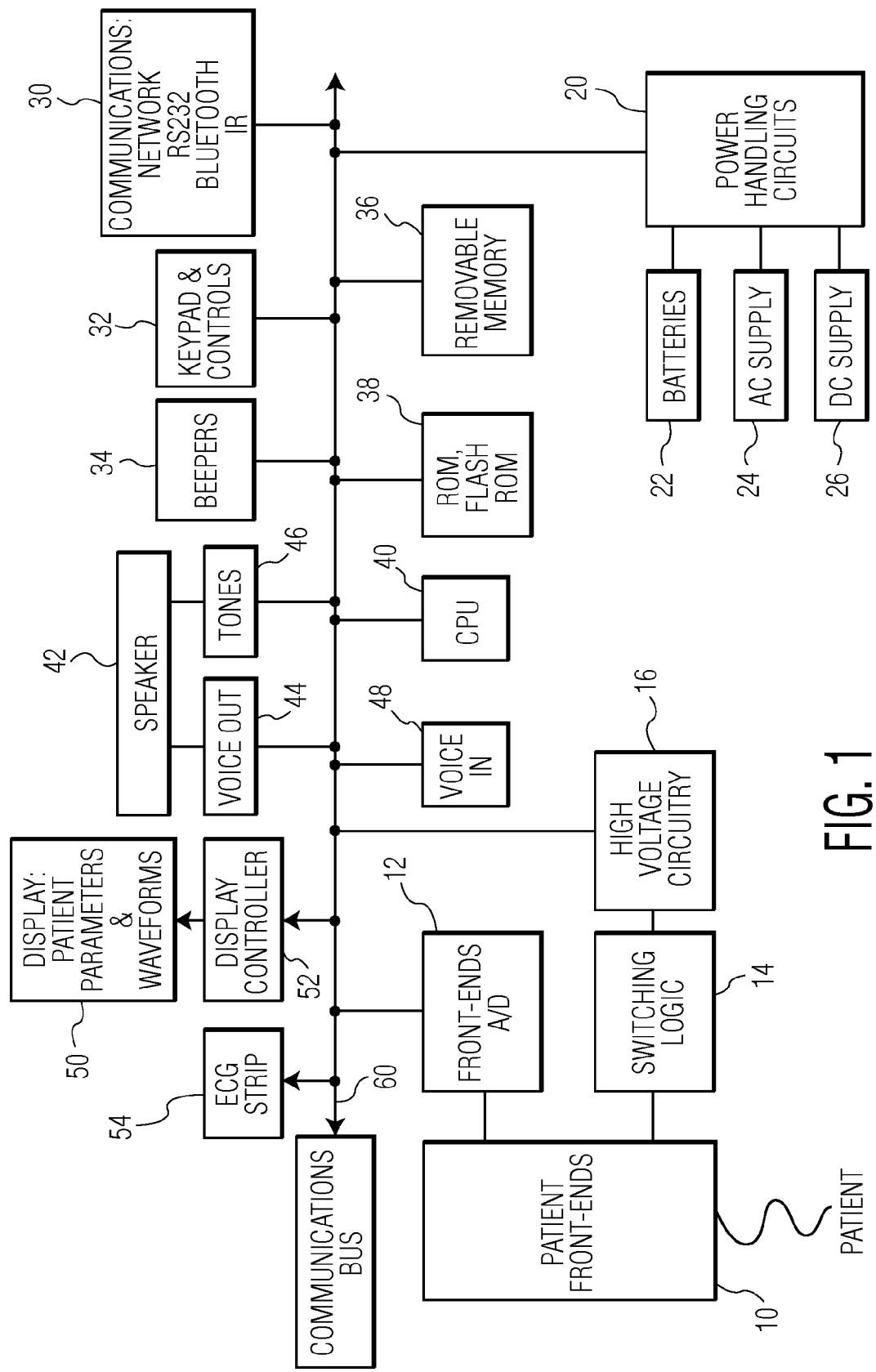
FIG. 1 illustrates in block diagram form a defibrillator/monitor constructed in accordance with the principles of the present invention.

Referring first to FIG. 1, a patient monitor/defibrillator constructed in accordance with the principles of the present invention is shown in block diagram form. The instrument shown in FIG. 1 is commercially available from Philips Healthcare of Andover, Mass. as the MRx defibrillator/monitor and is capable of performing defibrillation of a patient who is experiencing ventricular fibrillation. It is also capable of performing ECG monitoring including the cardiac monitoring necessary for automatic defibrillation analysis and myocardial infarction decision-making. The illustrated monitor is also capable of $SpO_2$ oxygen sensing, noninvasive blood pressure monitoring, and end tidal $CO_2$ monitoring. Other functions such as invasive blood pressure monitoring and patient temperature monitoring may also be found in such a multi-functional instrument.

The monitor/defibrillator has a plurality of patient front-ends, which are input circuitry for the sensors attached to the patient. This circuitry includes conventional sensing and amplification circuitry for ECG electrodes, for oxygen sensors, for pressure sensing and for carbon dioxide sensing, among others. The information received by the patient sensors and the front-end circuitry 10 is digitized by front-end A/D converters 12 if the signals are not already in digital form. The digitized information is coupled to processing circuitry of the instrument by a communications bus 60 which connects data between the various modules of the instrument.

The monitor/defibrillator instrument includes high voltage circuitry 16 for defibrillator operation. The high voltage circuitry produces the high voltage pulses necessary for defibrillation which are connected at the appropriate times by switching logic 14 to defibrillator electrodes coupled to the patient. This circuitry provides the high voltage shocks needed to disrupt the ventricular fibrillation and return the heart to a normal rhythm. The shock level and waveform delivered for defibrillation can be automatically calculated by a processor in the monitor or can be manually set with the controls of the instrument by an experienced medical technician or physician.

Power for the modules within the monitor/defibrillator instrument is distributed by power handling circuits 20. The power handling circuits 20 will distribute power from batteries 22, from an AC supply 24, or from a DC supply 26. The AC and DC supplies are also coupled to circuitry which charges the batteries when the monitor is powered from these external power sources.

The information obtained by the instrument may be sent to other instruments or locations by communications circuitry 30. This may include a network connection, an RS232 connection, and/or a wireless connection (e.g. Bluetooth, WiFi or infrared, etc.)

The monitor/defibrillator instrument is operated and adjusted by means of a keypad and controls 32. In a constructed embodiment the keypad is a membrane keypad providing integrity against environmental conditions. Controls such as an on/off switch, power level and shock delivery controls for defibrillation, a printer, and other functions may also be provided.

The monitor/defibrillator is operated under control of a central processing unit (CPU) 40. The CPU runs software stored on a read-only memory (ROM) 38, including standard ECG, ACI-TIPI, and TPI analysis software. Flash ROM is also provided for the control of feature setups and new or special capabilities such as waveform information. Removable memory 36 is provided for storage of information generated during a patient episode. Patient information such as cardiac waveforms before and after defibrillation and ECG analysis reports are also stored on the removable memory 36, which can be removed and given to a subsequent care-giver for review, record-keeping, and subsequent diagnosis. The removable memory 36 can also record voice information from a care-giver speaking into a microphone 48.

Beepers 34 are used to drive a solid-state sound source that produces short "chirping" sounds. These sounds indicate that the instrument's resident self-test has detected a low battery level or a malfunction in a patient-critical circuit group. There is also a dedicated display on the front of the instrument that presents a large, flashing, red X to indicate a low battery level or a large, fixed, red X to identify a circuit failure.

Tones 46 are produced by the software and then used to drive the speaker 42. This capability is used during certain monitoring functions such as in the production of a short tone in response to each heart cycle. Combinations of tones are used to issue audible alerts and alarms when a patient's vital measurements fall outside the alarm limits selected. The speaker 42 can reproduce pre-recorded voice instructions and information stored and reproduced from voice-out circuitry 44. A display 50 is provided for the display of patient information such as physiological measurement parameters and waveforms and the display screens discussed below. The display 50 also displays input data and the results of ECG analysis, predictive ACI-TIPI ischemia analysis and TPI analysis in accordance with the present invention. An ECG strip printer 54 prints ECG output information including acquired ECG traces and the results of ECG analysis, ACI-TIPI analysis, and TPI analysis.

In an implementation of the present invention, the patient's ECG data is acquired by a 12-lead ECG system coupled to the front-end circuitry 10 of the MRx defibrillator/monitor. The ECG data is applied as input data to a standard ECG analysis, the ACI-TIPI ischemia analysis, and TPI analysis software programs. In accordance with the present invention, the standard ECG analysis software provides an indication of an abnormal condition such as acute MI and the ACI-TIPI program calculates the predicted probability of acute cardiac ischemia from the ECG data.

In past practice the cardiac analysis system would present a full ACI-TIPI report which includes the predicted probability of acute cardiac ischemia and a list of criteria that were used in the calculation of the probability. The disadvantage of this approach is that for small, pre-hospital devices, the screen size may not allow display of the full report, or the user must wait for the report to be printed. In accordance with a further aspect of the present invention, the MRx system can be configured to display the predicted probability of ACI with the standard ECG interpretation report. In addition, if the predictive value is greater than or equal to a threshold pre-set by the user, the value is highlighted with a colored background, drawing the attention of the clinician to the important finding. The advantage of this approach is that the clinician is more likely to immediately see the result and identify patients that need immediate intervention.

In an implementation of this feature, the user of an MRx system with the ACI-TIPI option can configure the system so that the ACI-TIPI analysis is performed on the 12-lead ECG data that is acquired. In addition, the user can configure an "ACI Threshold" setting, above which value the ACI prediction is highlighted. These configuration choices are stored in the internal file system of the MRx defibrillator/monitor.

If the MRx system is configured to perform ACI-TIPI analysis of a 12-lead ECG, then the Predicted Probability of Acute Cardiac Ischemia is displayed at the bottom of the MRx display before the printing of the report has completed. If the value of the predicted probability is less than the ACI threshold set previously by the user, the predicted probability is displayed with white text on a black background. If the predicted probability is greater than the ACI threshold, the predicted probability is highlighted by displaying it with white text on a red background. This is an unambiguous indication that the patient needs immediate intervention, such as an emergency catheterization.

The report can be printed, exported from the device for later review by transport of the removable memory 36, or transmitted by network or Bluetooth communications 30 and cell phone to a receiving care facility to prepare for treating an incoming patient.

Figure 2:
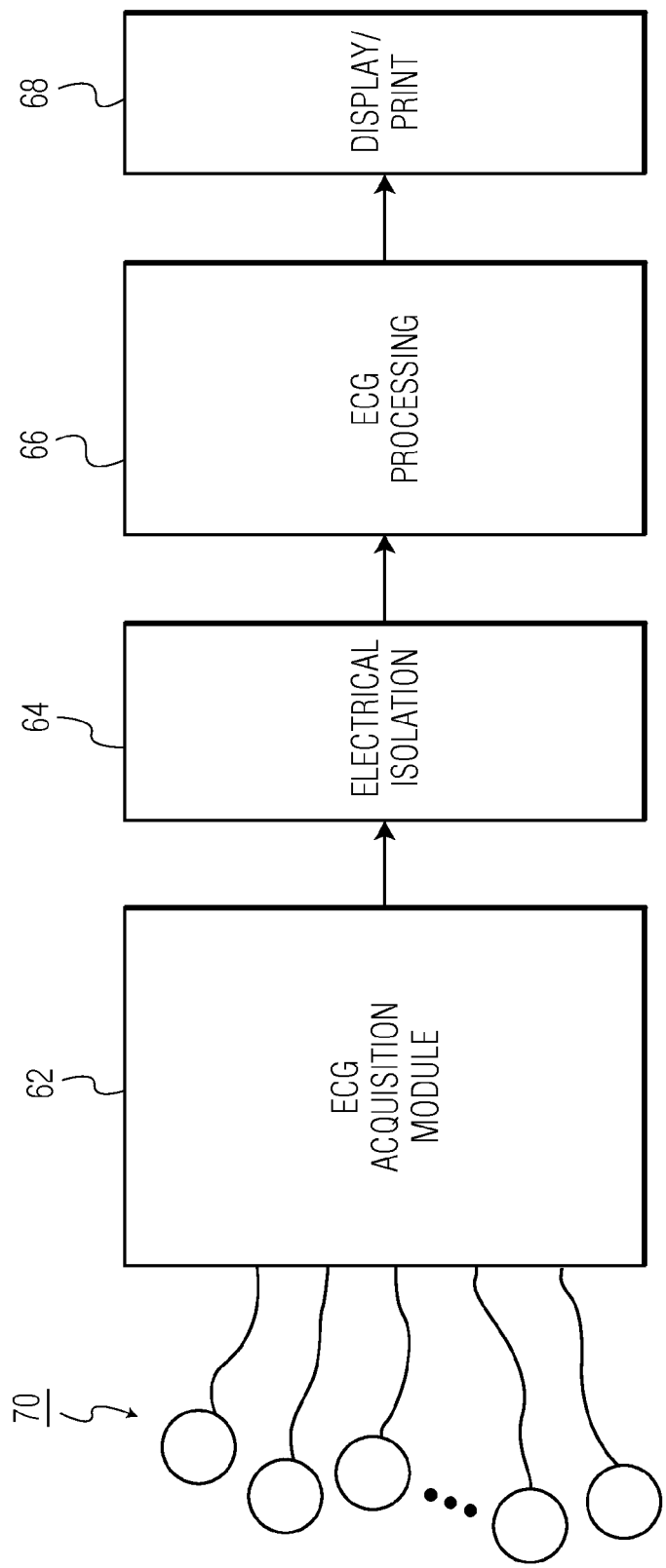
FIG. 2 is a block diagram of major subsystems of an ECG signal acquisition system constructed in accordance with the principles of the present invention.

Referring now to FIG. 2, an ECG signal acquisition system suitable for use in an implementation of the present invention is shown in block diagram form. A plurality of electrodes 70 are provided for attaching to the skin of a patient. Usually the electrodes are disposable conductors with a conductive adhesive gel surface that sticks to the skin. Each conductor has a snap or clip that snaps or clips onto an electrode wire of the ECG system. The electrodes 70 are coupled to an ECG acquisition module 62 of the acquisition system that preconditions the signals received by the electrodes. The electrode signals are coupled to an ECG processing module 66, generally by means of an electrical isolation arrangement 64 that protects the patient from shock hazards and also protects the ECG system when the patient is undergoing defibrillation, for instance. Optical isolators are generally used for electrical isolation. The processed ECG information is then displayed on an image display or printed in an ECG report by an output device 68.

Figure 3:
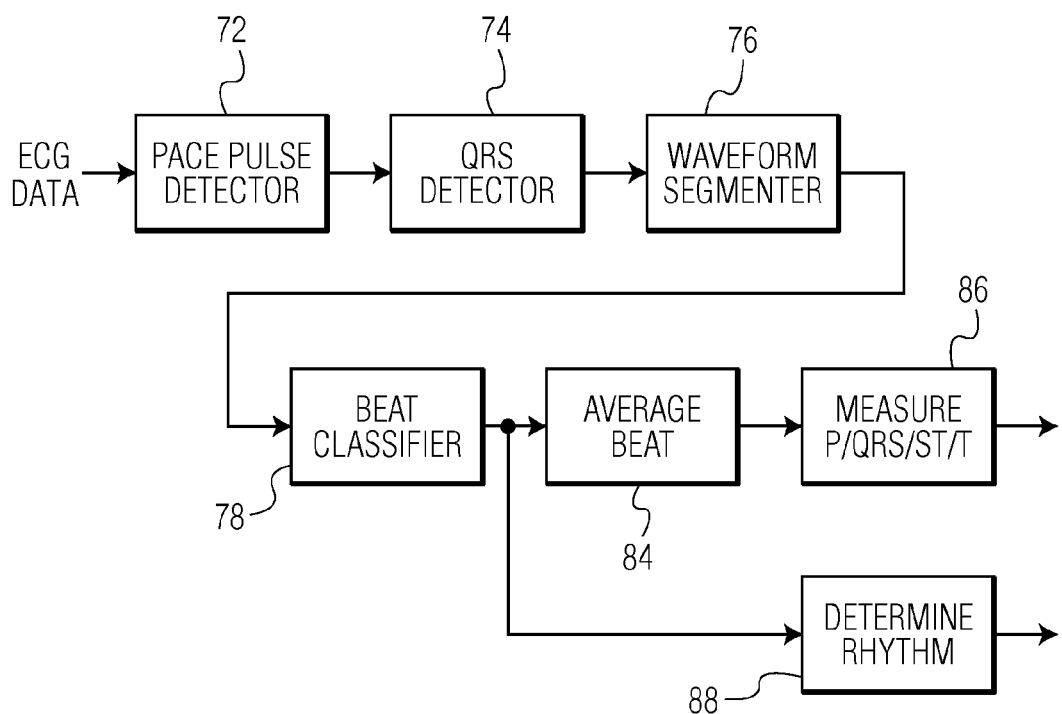
FIG. 3 is a block diagram of the processing module of the ECG system of FIG. 2.

FIG. 3 is a block diagram of the analysis portion of a typical ECG analysis system. A pace pulse detector 72 identifies and sets aside electrical spikes and other electrical abnormalities produced by a pacemaker for patients who are wearing one. A QRS detector 74 detects the dominant pulse of the electrical traces. FIG. 6a illustrates a typical normal ECG trace, where it is seen that the Q-R-S segments delineate the major electrical pulse of the trace, which is the pulse that stimulates a contraction of the left ventricle. Delineation of the QRS complex forms the basis for detecting the lesser perturbations of the trace, which is performed by the waveform segmenter 76. The waveform segmenter delineates the full sequence of trace segments including the P wave and the Q to U segments of the ECG trace including the S-T segment. With each waveform now fully delineated, a beat classifier 78 compares each new beat with previous beats and classifies beats as normal (regular) or abnormal (irregular) for the individual undergoing diagnosis. The classification of the beats enables an average beat analyzer 84 to define the characteristics of a normal heartbeat and the amplitudes and segment durations of an average beat are measured at 86. The beat classifications are used to determine the heart rhythm at 88.

Figure 4:
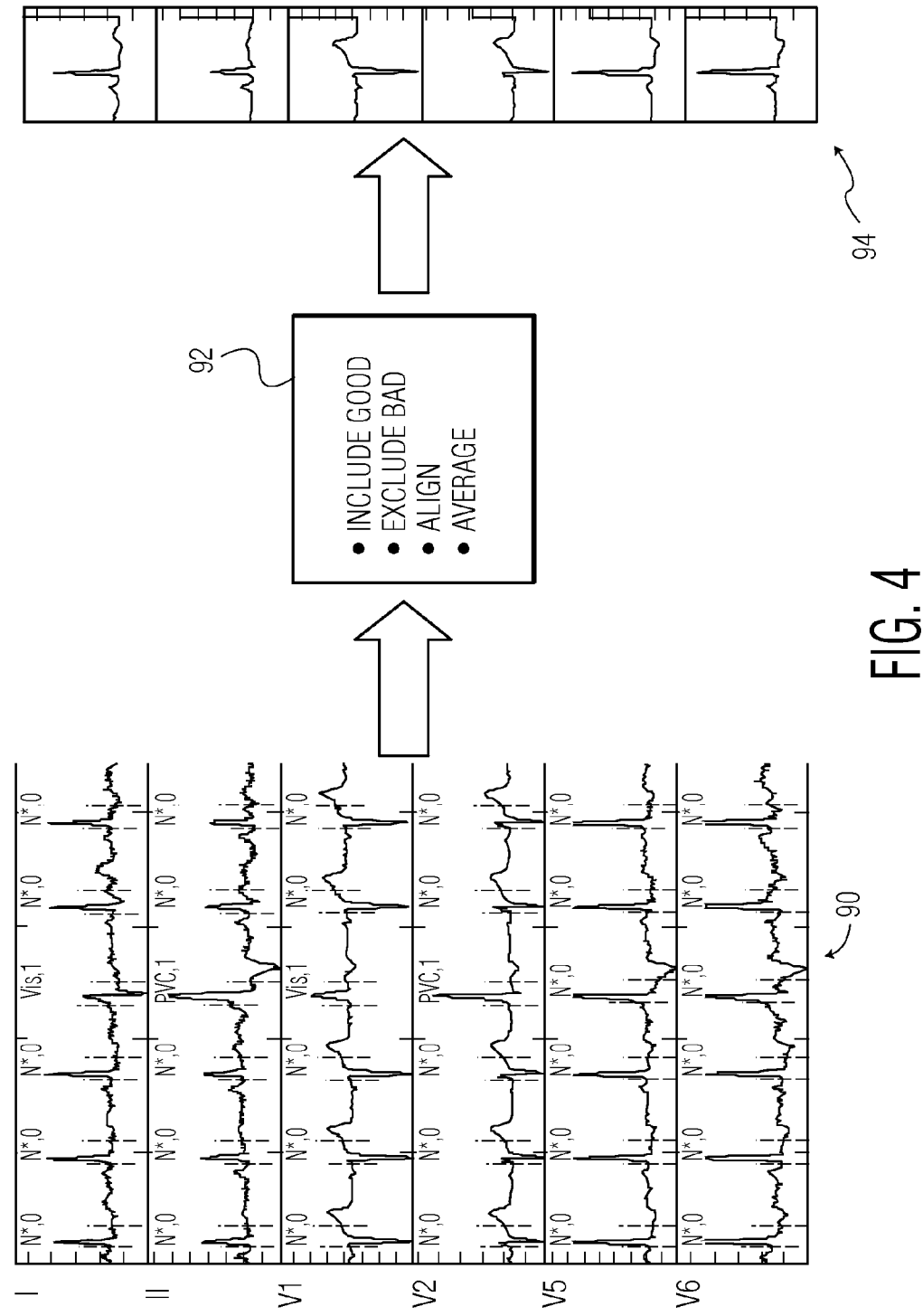
FIG. 4 illustrates the processing of ECG trace data to provide information about the heartbeat and its rhythm.
Figure 5:
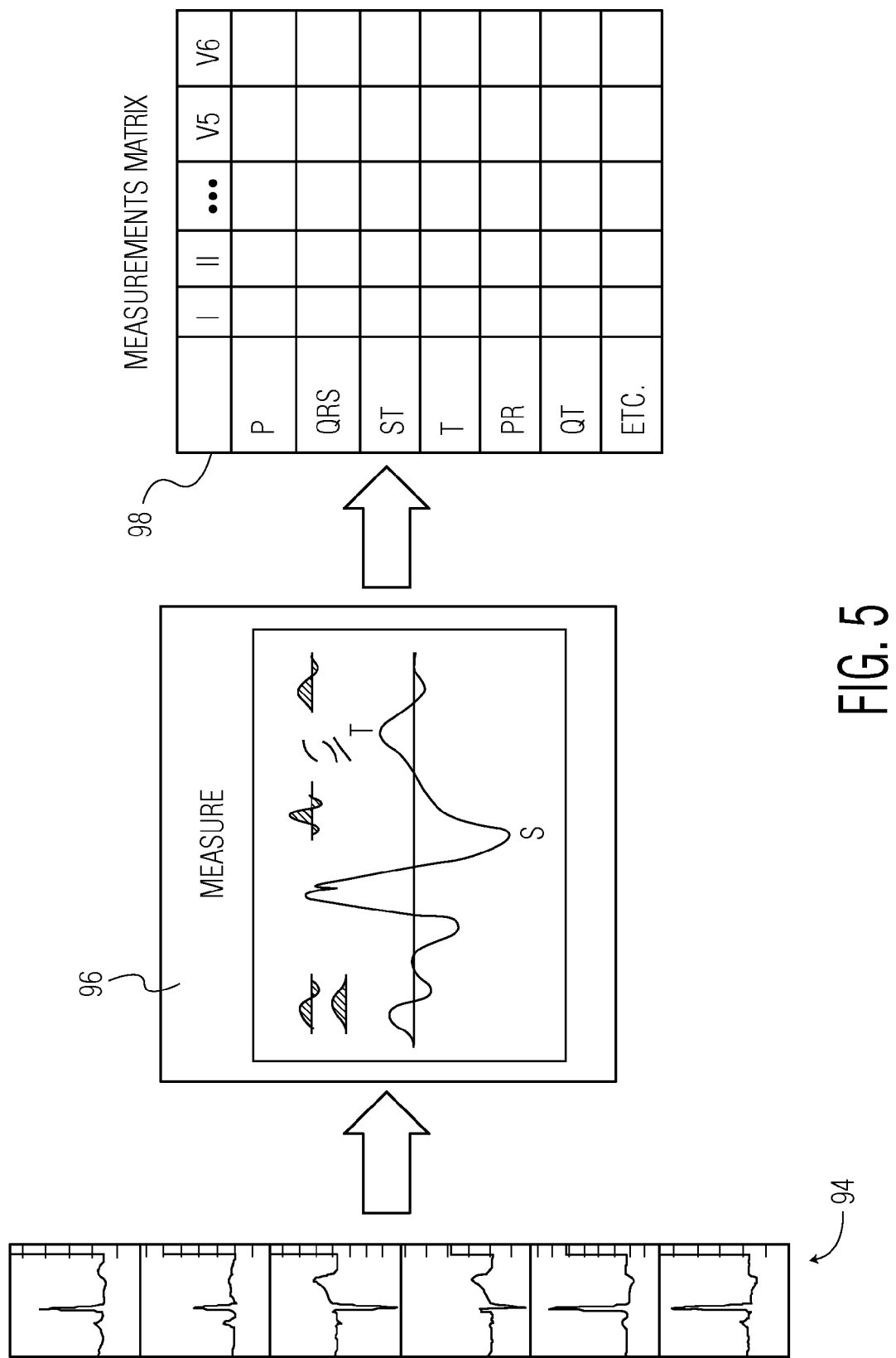
FIG. 5 illustrates the measurement of different parameters of an ECG trace.

FIGS. 4 and 5 are functional illustrations of some of this ECG trace processing. At the left side of FIG. 4 is a series 90 of ECG traces from ECG leads I, II, V1, V2, V5 and V6. The beat classifier 78 compares the various beat characteristics and has classified some of the beats as normal (N*,0). For example, all of the beats from leads V5 and V6 have been classified as normal. The other four leads contain a beat exhibiting the characteristics of premature ventricular contraction (PVC,1) in this example. At 92 the ECG system aggregates the characteristics of the normal beats, excludes characteristics of the abnormal beats, aligns the beats in time and averages them to produce an average beat. The traces at 94 illustrate the traces of an average beat for the six leads shown in this example. In FIG. 5 the average beat traces 94 of the six leads are measured for various characteristics shown at 96, such as the amplitudes and durations of the Q wave, the R wave, and the T wave and inter-wave intervals such as QRS, ST, and QT. The measurements are illustrated as recorded in a measurement matrix 98 for the six leads of this example. The ECG waves and their measurements can be sent to an offline workstation with a report generation package for the production of a report on the patient's ECG waveforms. In the implementation described herein, the MRx defibrillator/monitor has its own onboard ECG reporting package.

In an implementation of the present invention, ECG lead signals are analyzed for particular patterns of elevated and depressed ST segments which relate to stenoses of specific coronary arteries and branches which may have caused an infarction. In the normal ECG trace of FIG. 6a, the signal level of the ST segment 80 is at or very close to the nominal baseline of the ECG trace. When a coronary artery becomes fully occluded, the ST segment 82 for a lead in proximity to the artery will be highly elevated as shown in FIG. 6b, where the dashed line indicates the nominal baseline of the trace. The ST segment can be elevated 100 μvolts or more. ECG leads proximate to the other side of the heart will exhibit a corresponding depression, which can be detected and correlated with the elevated trace for correlating identification of the ST elevation. The amount of ST elevation will vary as a function of the time and degree of stenosis, which will be taken into consideration in the ECG analysis that produces the standard interpretive report.

FIG. 7 is a data flow diagram showing the development of standard ECG analysis, ACI-TIPI analysis, and thrombolytic predictive instrument (TPI) analysis and reporting by the MRx defibrillator/monitor. At 100 the system acquires ECG data, from which measurements are made at 102 as previously described. These measurements of the ECG signal are stored in the measurement matrix and used at 104 to generate standard ECG interpretive statements. Other inputs are shown for the standard interpretive statements, such as the patient sex and the patient age. These statements are then used to build an ECG report at 110. The ECG measurements are also used in conjunction with other inputs such as patient sex, age, and chest pain symptom information at 106 to generate ACI-TIPI statements for the ECG report. The ECG measurements are further used with patient sex, age and weight data and other user inputs such as time since the onset of symptoms, blood pressure, history of hypertension, and history of diabetes at 108 to generate TPI statements. Some or all of these statements will then be incorporated into the printed or electronically stored or transmitted report at 110.

FIG. 8 is a flowchart showing the sequencing of various ECG analyses, including conditional ACI-TIPI analysis. At 112 the ECG analysis system acquires ten seconds of a patient's ECG data. This data is used at 114 to make the ECG measurements as described above. At 116 the system performs the standard ECG analysis including the generation of the standard interpretations. Standard ECG analysis algorithms are described, for example, in the *Philips DXL ECG Algorithm Physician's Guide,* published by Philips Healthcare of Andover, Mass. (2009), which explains the diagnoses resulting from various ECG characteristics. The system then checks to see whether the user has set the system to perform an advanced measurement mode of analysis. If no advanced mode has been set, the sequence at 126 goes to 156 to display and print the ECG report. Another possibility is that the ECG analysis system has been set to always run ACI-TIPI analysis. In that case, the system will generate ACI-TIPI interpretation statements at 130. The ACI-TIPI analysis aids a physician's diagnosis of indications of angina pectoris and acute myocardial infarction by computing a predicted probability of acute MI in the form of a 0-100% percentage score. This score is generated by a formula based on weighted values for the patient's age, sex, chest pain status, and selected ECG measurements (significant Q waves, ST segment elevation or depression, and T wave elevation or inversion. An equation uses these measurements and characteristics to compute the predicted probability of acute MI. Further details of this equation and its computations can be found in the *Predictive Instruments Physician's Guide,* published by Philips Healthcare of Andover, Mass. (2002).

In addition to setting the system to run ACI-TIPI, the user may also set the system to run TPI analysis. If this setting has been selected, the system will generate ACI-TIPI interpretation statements at 140 and then perform TPI screening analysis at 142 to assess whether the presented ECG is a candidate for TPI analysis. If this assessment at 132 is affirmative, the system will prompt the user to input the TPI inputs at 134, as described above in FIG. 7. In accordance with a further aspect of the present invention, the system may also solicit thrombolytic therapy contraindications from the user at 136. The TPI analysis will then generate TPI interpretation statements at 138. Similar to ACI-TIPI, the TPI analysis computes predicted probabilities of patient outcome and risk associated with thrombolytic therapy in the form of a 0-100% percentage score. The score is generated using a formula based on weighted values for the patient's age, gender, weight, blood pressure, time since the onset of ischemic symptoms, medical history, and ECG waveform measurements. Further details of TPI analysis may be found in the Predictive Instruments Physician's Guide referenced above.

In accordance with the principles of the present invention, when the user has set the system for conditional ACI-TIPI analysis, the system first looks at the standard ECG analysis at 120 to see if the ECG was found to be normal. If the answer is "no", then the system checks at 122 whether the results of the standard analysis found acute MI to be indicated. If the answer to this inquiry is also "no", then ACI-TIPI analysis is performed at 124.

In accordance with a further aspect of the present invention if, at the end of the foregoing analyses a predicted probability of acute MI was computed by ACI-TIPI analysis and found at 150 to be in excess of a preset threshold, then the background for the ACI message is set to red at 154 to highlight it to the attention of the physician. If the predicted probability is below the threshold, the background for the ACI message is set to black at 152. The report screen is displayed on the display of the ECG analysis system at 156 and, if desired, the 12-lead ECG report is printed at 160.

The following drawings illustrate exemplary report screens and printed reports that are produced in accordance with the present invention. FIG. 9 illustrates a report screen 170 that is produced when the standard ECG interpretation results in a definitive diagnosis of acute MI. This result may be produced if only the standard interpretation is used (box 126 of FIG. 8) with an appropriately diagnostic ECG, or the conditional ACI-TIPI analysis path is followed in FIG. 8, in which the ECG is found to be abnormal (120 is "no") and the standard interpretation results in a diagnosis of acute MI (122 is "yes"). Since the standard analysis has determined that the patient has acute MI, the ACI-TIPI analysis is not run. The report screen 170 shows relevant patient ECG measurements at the left side of the screen, specific diagnoses at the top center of the screen resulting in a determination of "ABNORMAL ECG" at the lower center and a final diagnosis of "Acute MI" at the bottom on the screen. A corresponding report is printed on the ECG strip 172 following the printout of the ECG traces (not shown), as shown in FIG. 10.

FIG. 11 illustrates a report screen 174 in another case where the conditional ACI-TIPI analysis path has been followed. In this case the standard analysis has found the ECG to be abnormal (120 is "no"), but the data is insufficient for the standard analysis to definitively determine acute MI (122 is "no"). It is seen that the standard analysis is reporting "Borderline ST elevation" at the top of the screen and a final determination of "BORDERLINE ECG". Under these conditions the ACI-TIPI analysis is run at 124 and in this case the ACI-TIPI analysis has found a "Predicted Probability of Acute Ischemia 60%" as shown at the bottom of the screen. The clinician is thus given a definitive indication that acute ischemia may be present. FIGS. 13*a* and 13*b* show segments of the printed report for this patient, with segment 180 in FIG. 13*a* illustrating the printed report from the standard ECG analysis and segment 182 in FIG. 13*b* illustrating the printed report of the ACI-TIPI analysis, including the patient characteristics which were weighed in making the probability determination.

FIG. 12 shows a report screen 176 which may result from following any of the ACI-TIPI analysis paths in FIG. 8. In this example the user had set a threshold of a predicted probability of 75% above which the ECG analysis system will highlight the probability finding. It is seen that the report screen 176 is reporting a predicted probability of acute ischemia of 82%, which is in excess of this preset threshold. In this case, boxes 150 and 154 cause the final diagnosis to be highlighted to draw the attention of the physician, and the predicted probability and diagnosis of acute MI both appear against a highlighted background 178.

FIG. 14 shows an exemplary report screen 182 which illustrates the problem that can arise when the ACI-TIPI analysis is run as a mandatory part of the sequence. In this case the standard ECG analysis has found the ECG to be abnormal and has determined that "Acute MI" is present, as shown at the bottom of the screen. The ACI-TIPI has also been run and results in a predicted probability of acute ischemia of 37%. Now the clinician is presented with a quandary in how to triage the patient: is acute MI present or not? The conditional ACI-TIPI analysis path, which runs the ACI-TIPI analysis only when the standard analysis is inconclusive, will prevent this problem from arising.

The ECG analysis sequence of FIG. 8 may also run thrombolytic predictive instrument (TPI) analysis to assist a physician in assessing patient risk and outcome when treated with thrombolytic therapy such as blood thinners. Certain information about the patient is used by the TPI analysis as shown in FIG. 7 and described above in conjunction with FIG. 8. This patient information is input into the ECG analysis system by the user as stated in box 134 of FIG. 8 and illustrated by display screen 190 of FIG. 15, which shows that this patient data has been entered into the system. In accordance with a further aspect of the present invention, the user is also presented with contraindications to thrombolytic therapy to consider before prescribing the therapy. This is illustrated by display screen 192 of FIG. 16, in which the user is presented with a list of factors to consider which, in this example, can be answered by "yes", "no", or "unknown". FIG. 16 shows a list of nine such factors, including one of which is highlighted for response by the user. When the list of contraindication factors is first presented to the user, all of the answers are shown as "unknown." Thus the user can see at a glance which questions in the list remain to be answered by "yes" or "no" when the user has that information.

In accordance with yet another aspect of the present invention, the list of contraindications is programmable by a user. A medical institution may want its attending physicians to only consider certain contraindications, for example, or may want its physicians to always consider specific contraindications. These contraindications can be selectively programmed into the ECG analysis system list of FIG. 16 so that an attending physician is always presented with the contraindications to be considered at the institution. For example, in a constructed embodiment the system comes from the manufacturer with a default list of contraindication which is:

1. Right vs. left arm sys. BP difference>15 mmHg
2. History of structural central nervous system disease
3. Significant closed head/facial trauma within prey. 3 mos.
4. Major trauma, surgery, GI/GU bleed within 6 wks
5. Bleeding or clotting problem or on blood thinners
6. CPR for longer than 10 min.
7. Pregnant female
8. Serious systemic disease
9. Pulmonary edema
10. Signs of shock A user who wants to edit the list displays the current list of contraindication as shown in FIG. 16 and clicks on an edit button on the screen to enter a special configuration mode. After editing the list to contain the desired contraindications, the user saves the edited list and exits the configuration mode. Thereafter the user is presented with the customized contraindications each time the contraindications screen is used. Users may alter, delete, replace or supplement any of the default contraindications with other contraindication factors they may favor, such as:

History of stroke or brain surgery
Acute trauma of any kind
Anticoagulant medications (coumadin, warfarin, heparin)
Known bleeding problems
Any GI bleeding in last 12 months
Any surgery in last two months
Terminal cancer
Significant liver or kidney disease A physician or medical institution may thus customize the list of contraindication considerations to conform with the factors they want to consider for the best and most appropriate patient care.

FIGS. 17a, 17b, and 17b illustrate three ECG strip segments on which TPI results are printed. The segment 194 in FIG. 17a shows the patient data which was input for the TPI analysis. Segment 196 in FIG. 17b shows the results of TPI analysis as TPI statements, the predicted outcomes when treating this patient with thrombolytic drugs. Segment 198 of FIG. 17c shows the contraindication factors considered by the physician and the answers input into the system in response to the contraindication questions.

In the MRx system implementation of the present invention, all of the information of the printed reports illustrated above can also be electronically communicated to other computer-based instruments, as by Bluetooth communication shown in box 30 of FIG. 1.

What is claimed is:

1. An ECG analysis system which analyzes patient ECG data comprising:
 a standard ECG analysis processor adapted to analyze ECG data to produce a result output indicating whether a myocardial infarction (MI) is indicated;
 an ischemia predictive indicator processor, responsive to patient characteristic data, and adapted to analyze patient characteristic data and ECG data to produce a result output indicating the probability of a myocardial infarction; and
 a processor sequence setting by which operation of the ischemia predictive indicator processor is conditioned upon the result output of the standard ECG analysis processor,
 wherein the processor sequence setting prevents the ischemia predictive indicator processor from presenting its result output to a user in direct response to the processor sequence setting determining that the result output of the standard ECG analysis processor indicates that acute MI is present or in direct response to the processor sequence setting determining that the ECG is normal.

2. The ECG analysis system of claim 1, further comprising a display on which result outputs of the standard ECG analysis processor and the ischemia predictive indicator processor are displayed.

3. The ECG analysis system of claim 1, further comprising an ECG strip printer adapted to print ECG output data including result outputs of the standard ECG analysis processor and the ischemia predictive indicator processor.

4. The ECG analysis system of claim 2, further including a probability threshold setting operable by a user to set a threshold above which the result output of the ischemia predictive indicator processor is highlighted on the display.

5. The ECG analysis system of claim 1, further comprising a second processor sequence setting which causes the ischemia predictive indicator processor to present its result output to a user regardless of the result output of the standard ECG analysis processor.

6. The ECG analysis system of claim 1, further comprising a thrombolytic therapy predictive indicator processor which produces a result output of a possible outcome of thrombolytic therapy; and
 further comprising a third processor sequence setting which causes the ischemia predictive indicator processor and the thrombolytic therapy predictive indicator processor to present their result outputs to a user when the thrombolytic therapy predictive indicator processor indicates that the patient ECG data is suitable for thrombolytic therapy predictive analysis.

7. The ECG analysis system of claim 1, wherein the processor sequence setting causes the ischemia predictive indicator processor to present its result output to a user when the result output of the standard ECG analysis processor does not indicate that acute MI is present.

8. The ECG analysis system of claim 2, wherein the display is further responsive to a user control for inputting patient characteristic data into the ECG analysis system.

9. A method for analyzing patient ECG data comprising:
 analyzing ECG data with a standard ECG analysis processor to produce a result output indicating whether a myocardial infarction (MI) is indicated;
 and, conditioned upon the result output of the ECG data analyzing by the standard ECG analysis processor,
 analyzing patient characteristic data and ECG data with an ischemia predictive indicator processor to produce a result output indicating the probability of a myocardial infarction; and
 visually presenting one or more result outputs,
 wherein analyzing with the ischemia predictive indicator processor is inhibited in direct response to the processor sequence setting determining that the result output of the standard ECG processor indicates that the ECG is normal.

10. The method of claim 9, further comprising:
 inputting patient characteristic data for use by the ischemia predictive indicator processor.

11. The method of claim 9, wherein visually presenting presents only the result output of the standard ECG processor when the standard ECG processor indicates that acute MI is present.

12. The method of claim 9, wherein visually presenting presents the result outputs of both the standard ECG processor and the ischemia predictive indicator processor when the result output of the standard ECG processor is not definitive as to the presence of acute MI.

13. The method of claim 9, wherein visually presenting presents one or more result outputs on at least one of a video display and a printed ECG strip.

* * * * *